Figure 1:
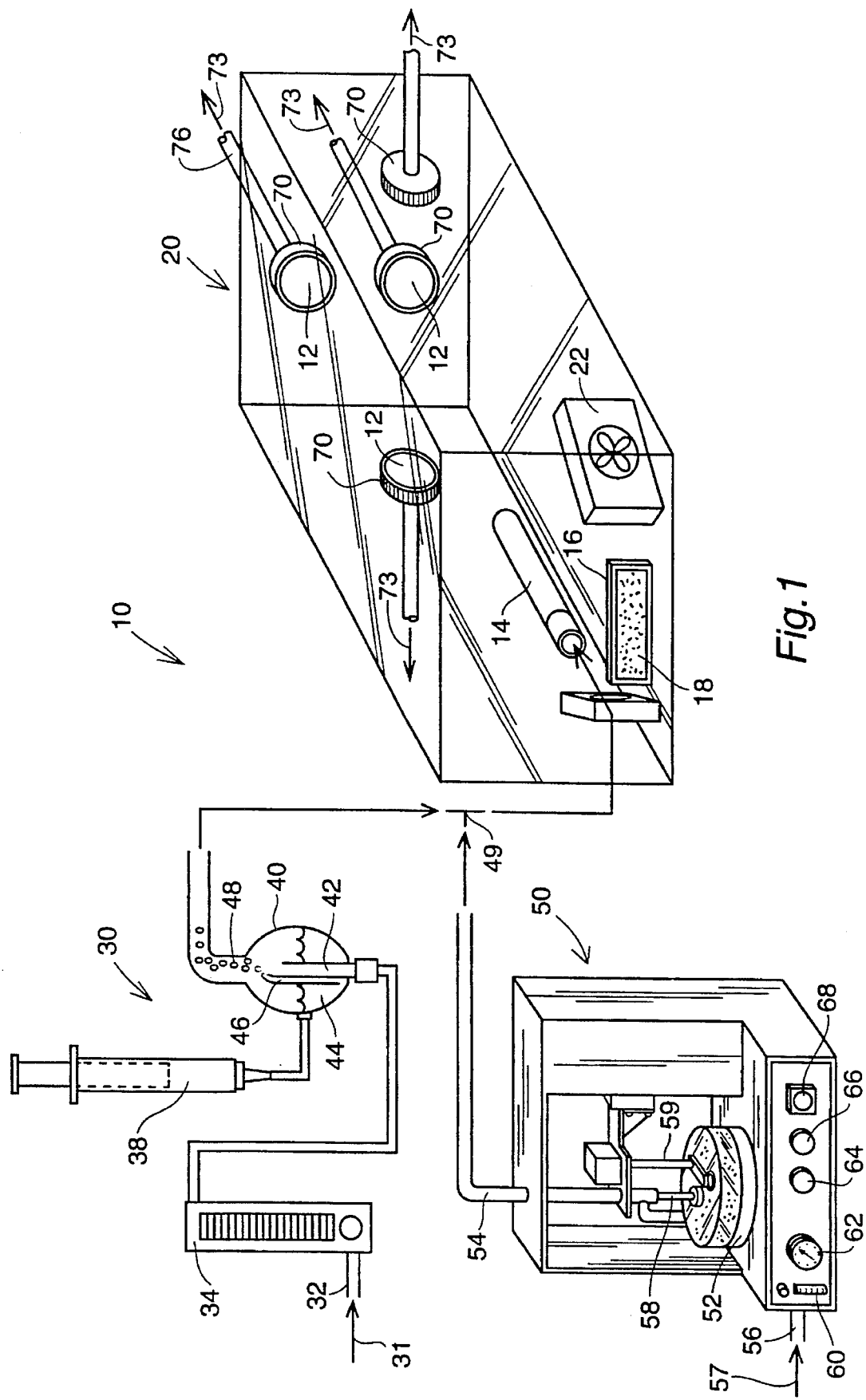

United States Patent [19]

Miller et al.

[11] Patent Number: 5,502,998

[45] Date of Patent: Apr. 2, 1996

[54] DEVICE AND METHOD FOR THE SIMULATION OF SAMPLES OF AIRBORNE SUBSTANCES

[75] Inventors: Larry S. Miller, Columbus; Ken W. Lee, Powell; Doyle F. Kohler, Columbus; Randy Jones, Delaware; Richard Tuttle, Columbus, all of Ohio

[73] Assignee: The Procter and Gamble Company, Cincinnati, Ohio

[21] Appl. No.: 232,508

[22] Filed: Apr. 25, 1994

[51] Int. Cl.⁶ .................................................. G01N 17/00
[52] U.S. Cl. .................. 73/1 G; 73/865.6; 73/863.81; 73/863.23
[58] Field of Search ................. 73/1 G, 863.23, 73/863.81, 865.6

[56] References Cited

U.S. PATENT DOCUMENTS

| | | | |
|---|---|---|---|
| 2,672,431 | 3/1954 | Goetz | 73/61.72 |
| 2,970,468 | 2/1961 | Price | 73/61.41 |
| 3,149,775 | 9/1964 | Pagano | 73/865.6 |
| 3,888,112 | 6/1975 | De Leeuw et al. | |
| 4,004,882 | 1/1977 | Byrne et al. | 73/863.23 |
| 4,269,057 | 5/1981 | Ong et al. | 73/1 G |
| 4,930,359 | 6/1990 | Wolfrum et al. | 73/863.23 |
| 5,005,403 | 4/1991 | Steudle et al. | 73/61.71 |
| 5,054,309 | 10/1991 | Mettes et al. | 73/1 G |
| 5,088,316 | 2/1992 | McKelvey et al. | 73/865.6 |
| 5,163,332 | 11/1992 | Wong | 73/863.23 |
| 5,255,556 | 10/1993 | Lobdell | 73/31.02 |
| 5,259,254 | 11/1993 | Zhu et al. | 73/863.23 |
| 5,307,018 | 4/1994 | Gadgil | 73/865.6 |

FOREIGN PATENT DOCUMENTS

| | | | |
|---|---|---|---|
| 147040 | 11/1981 | Japan | 73/865.6 |
| 131051 | 6/1988 | Japan | 73/865.6 |
| 272937 | 10/1989 | Japan | 73/863.23 |
| 1328730 | 8/1987 | U.S.S.R. | 73/863.23 |
| 1392502 | 4/1988 | U.S.S.R. | 73/1 G |

*Primary Examiner*—Hezron E. Williams
*Assistant Examiner*—Daniel S. Larkin
*Attorney, Agent, or Firm*—Philip J. Pollick

[57] ABSTRACT

An air sampling device and method to produce simulated samples of airborne substances obtained from institutional and industrial facilities. The device features 1) an environment container, 2) an ejector for introducing a contaminant into the container environment, 3) a sample collection holder to hold a filter, 4) a pump to withdraw the container environment and contaminant out of the container in a fashion that allows collection of the contaminant on the filter, and 5) a container inlet to allow replacement environment to enter the container.

30 Claims, 4 Drawing Sheets

DEVICE AND METHOD FOR THE SIMULATION OF SAMPLES OF AIRBORNE SUBSTANCES

BACKGROUND OF THE INVENTION

1. Field of the Invention

This invention relates to simulated samples of airborne substances found at facility sites and more specifically to a device and method for introducing airborne solid or liquid contaminants or both into a controlled environment for the production of simulated samples that can be used in analytical method development and validation studies.

2. Background

Air samples containing dust and other substances from institutional and manufacturing facilities are currently used by industrial hygienists for monitoring air quality control. Air samples are collected at the facility site onto filters using high volume air sampling devices. These air samples are devoted to air quality monitoring programs and an abundant number of such air samples are not available for the development and validation of new analytical testing and monitoring methodologies.

In addition, manufacturing and other "on-site" samples may not contain the required substances or contain them in such minute or uncontrolled quantities as to be unsuitable for test and methodology development. Although it is possible to introduce the substance into the air at the on-site facility for the purpose of collecting a specific type of sample, this can involve closing the facility while sample introduction and preparation takes place or risking exposure of on-site facility workers to the particular substance under study. Neither of these alternatives are very satisfactory. In fact, in some cases neither alternative may be a viable option when the substance is a particularly toxic or otherwise dangerous material. In addition, it is often difficult to control and/or identify other co-substances that may also be present at a facility site when samples are taken. In a similar vein, it may be desirable to study the effects of one or more of these co-substances on the validity of an analytical method for a specific substance. Such combinations often are not available "on-demand" at a facility site.

A facility site typically does not afford a good source of the large number of samples with the variation in substance and co-substance concentrations required for new analytical method development and validation studies. A need exists for a device and method for simulating actual facility samples in large quantities with a wide range of substance and co-substance concentrations that does not require closing a facility site or risking worker exposure to the various substances required for testing and development of existing and new contaminant detection and evaluation methodologies.

SUMMARY OF THE INVENTION

Accordingly, it is an object of this invention to provide a device and method for preparing simulated samples that have the essential features of an on-site sample including various airborne substances and materials that might be found in an on-site setting. As used here, the words "simulated sample" mean a sample that imitates and has many, if not all, of the important characteristics of an actual manufacturing site sample except for the fact that it is not produced at or taken from an actual facility site nor does it use materials and substances taken from the facility site. A "contaminant" is any material or substance that is not taken from the facility site that is used to produce the simulated sample. A "co-contaminant" is any material or substance that is not taken from the facility site that is combined with the contaminant to produce the simulated sample. Co-contaminants are especially useful in studying their effects on a specific contaminant testing and analysis methodology. For example, if the contaminant is an enzyme that simulates detergent enzymes found in the air at a detergent factory, it may be desirable to know the effect of surfactants and bleaching powders that might also be found in the air at the detergent factory on a testing procedure for the enzyme. The surfactant or bleaching powder that simulates the surfactant or bleaching powder found at the factory site and that is combined with the contaminant, i.e., the enzyme, to produce a simulated sample is referred to here as the co-contaminant. An "unwanted contaminant" is defined as an unwanted or undesirable substance or material that may find its way into the simulated samples as a result of being present at the site of the preparation of the simulated sample. For example, it might be an unwanted material in the air at the simulated sample production site or in one of the pressurized gases used in handling the contaminants and co-contaminants.

This invention features a container with entrance and egress passages for expelling or withdrawing and replacing the container environment. Typically the container environment is air but other gases and gas mixtures may be used. A contaminant injector is used to introduce an airborne contaminant or co-contaminant into the container environment. The term "injector" includes a wide variety of devices and methods for introducing solid and liquid airborne contaminants or co-contaminants into the container environment such as eductors, nebulizers and dust generators. A sample holder, typically a filter holder for securing (holding) a filter, is attached to the container in a fashion that allows a simulated sample of air-borne contaminant to be collected as the container environment moves out of the container.

The present device has the advantages of allowing the production of a large number and variety of contaminant samples in a controlled and "on demand" fashion that avoids the uncertainties and disruptions associated with on-site sample production while affording air-borne contaminant samples that have the composition and appearance of actual air samples. It has the advantage of allowing the preparation of samples without work-site disruption and downtime or the exposure of workers to substances that might not be otherwise present at the work site. It has the distinct advantage of allowing the preparation of samples of hazardous materials whose presence or introduction into the work-site environment would be impermissible, for example, dangerous chemicals, viruses, bacteria, and allergens, that might be found at facilities such as those associated with the detergent, food, health care, consumer product, chemical, pharmaceutical and biopharmaceutical industries. The device has the further advantage of being economical to construct and easy to operate. By affording simulated sample preparation at a laboratory site, this invention has the further advantage of obviating unnecessary handling, packaging and transport that occur when "on-site" samples are shipped to an off-site research facility.

Another object of this invention is to preclude the introduction of unwanted contaminants into the contaminant samples. To achieve this object, this invention features the use of a filter in conjunction with the replacement environment that enters the container. The use of such a filter has the advantage of precluding the introduction of unwanted contaminants that might otherwise be present in the replacement environment.

Another object of this invention is to provide known and accurate amounts of contaminant sample. In working with a contaminant sample, it is desirable to know the weight of the sample or components thereof (contaminants and co-contaminants) that are collected on a collection device such as a filter. Typically this is determined by weighing the filter before and after the collection of a contaminant sample or contaminant sample component.

Filters are often held in their holders by means of an O-ring and holding ring that compresses the O-ring against the filter in order to secure the filter to the filter holder. The compression can result in small portions of the filter adhering to the O-ring which results in an understatement of sample weight. A feature of this invention is the use of a washer made of a "non-stick" material such as polyethylene between the O-ring and filter. This has the advantage of providing accurate sample weights by avoiding loss of filter material as a result of adherence to the O-ring.

Another objective of this invention is to avoid unnecessary and difficult manipulation of the device when handling and changing sample filters and cleaning and servicing the interior of the container. To meet these objectives, the invention features the use of a resilient stopper with an aperture into which the tubular lower section (stem) of a filter holder is inserted. The resistant stopper with inserted filter holder is then inserted into an aperture in the air sampling container. This has the advantage of allowing quick access to the filter holder for easy insertion and removal of the filter.

For easy access to the interior of the container, this invention features a removable portion such as an end, side or top. This portion is attached to the remaining portion of the container with an intervening resilient sealing material that seals the container interior from the external environment.

Another object of this invention is to provide a multiple number of samples with a uniform weight and composition. To achieve this object, this invention features the use of a cylindrical container in which the filter holders are arranged near one end of the container on a circumference of the cylinder with an equal distance between each filter holder. Preferably the replacement environment and contaminant material enter the container at the center (on the cylinder axis) of the end of the cylinder opposite the filter holders. This has the advantage of providing an equidistant path from the point of contaminant introduction to each of the filters thereby providing a uniform distribution of contaminant on each of the filters.

For non-symmetrical containers, this invention features the use of a fan placed within the container. This has the advantage of providing uniform mixing of the contaminant with the container environment thereby providing uniform distribution on each filter in an arrangement where multiple filters are used. To further improve the contaminant distribution when a plurality of filters are used, a flow regulator is inserted between the filter holder and a container environment withdrawing device such as a vacuum pump or water aspirator. This allows for adjustment of the flow rates at each of the filters to a uniform flow rate, thereby, improving sample weight and uniformity of each of the samples.

The foregoing and other advantages of the invention will become apparent from the following disclosure in which one or more preferred embodiments of the invention are described in detail and illustrated in the accompanying drawings. It is contemplated that variations in procedures, structural features and arrangement of parts may appear to a person skilled in the art without departing from the scope of or sacrificing any of the advantages of the invention.

BRIEF DESCRIPTION OF THE DRAWINGS

FIG. 1 is a perspective view of one embodiment of this invention illustrating a square container and a nebulizer and dust generator.

FIG. 2 is a cross section of a filter holder illustrating the use of a washer to prevent sticking of filter particles to the O-ring.

FIG. 3 is a top view of the filter holder shown in FIG. 2.

FIG. 4 is another embodiment of this invention, the preferred embodiment, which uses a cylindrical container with at least one end of the container equipment for easy access to the container interior.

FIG. 5 is a cross section of the cylindrical container shown in FIG. 4.

FIG. 6 is a cross section of the cylindrical container shown in FIG. 4 illustrating the arrangement of a plurality of filter holders.

FIG. 7 presents graphs of various amounts of collected contaminant with respect to a contaminant variable. Specifically, FIG. 7A gives the amount of enzyme sample collected with respect to the concentration of an enzyme solution introduced into a nebulizer. FIG. 7B gives the amount of detergent sample collected with respect to the concentration of a detergent solution introduced into a nebulizer. FIG. 7C gives the amount of dust sample collected with respect to dust collection time.

In describing the preferred embodiment of the invention which is illustrated in the drawings, specific terminology is resorted to for the sake of clarity. However, it is not intended that the invention be limited to the specific terms so selected and it is to be understood that each specific term includes all technical equivalents that operate in a similar manner to accomplish a similar purpose.

Although at least two embodiments including the preferred embodiment of the invention have been herein described, it is understood that various changes and modifications in the illustrated and described structure can be affected without departure from the basic principles that underlie the invention. Changes and modifications of this type are therefore deemed to be circumscribed by the spirit and scope of the invention, except as the same may be necessarily modified by the appended claims or reasonable equivalents thereof.

DETAILED DESCRIPTION OF THE INVENTION AND BEST MODE FOR CARRYING OUT THE PREFERRED EMBODIMENT

With reference to the drawings and initially FIG. 1, an air sampling device 10 for producing simulated samples is shown having a sampling container 20 with 1) a contaminant introduction inlet 14 (6" of ¾" diameter glass tubing) for introducing an air-borne contaminant into the container environment, 2) a sample collection holder 70 for holding a sample collector such as a filter 84 (see also FIGS. 2–3), 3) a vacuum pump 104 (FIG. 4) for moving the container environment and air-borne contaminant through holder 70 so as to collect the air-borne contaminant on filter 84

(container environment out flow indicated by arrows 73 in FIG. 1), and 4) an inlet 16 for allowing replacement environment to enter container 20.

The sampling container 20 is constructed from 3/8" plexiglass and is about 24" long×18" wide×15" high. A contaminant is introduced into container 20 through inlet 14 by means of various types of sample injectors including the nebulizer setup 30 and dust sample generator 50 shown in FIG. 1. Although the container environment is preferably withdrawn from container 20 by means of one or more vacuum pumps or similar suction devices, e.g., water aspirators, that create a negative pressure in container 20, the present invention also contemplates the use of a pressurized source to accomplish the same function, that is, the movement of container environment through a filter 84 to allow capture of the contaminant on filter 84. Thus the contaminant inlet 14 would be subjected to a positive pressure such as from a compressor or bottled (pressurized) gas to force the container environment and contaminant through filters 84. Check valves would be provided to prevent unwanted flow out of inlet 14 and holders 70 would be securely attached to container 20. Although the container environment is typically air, it is to be realized that a wide variety of other environments could be provided should the contaminant be unstable in air.

Replacement environment inlet 16 is preferably fitted with a glass fiber filter 18 to prevent unwanted contaminants from entering container 20. Although not specifically shown, it is to be realized that the pressurized air associated with contaminant input can and should be filtered if it is desirable to control fully the content of the simulated sample.

Figure 4:
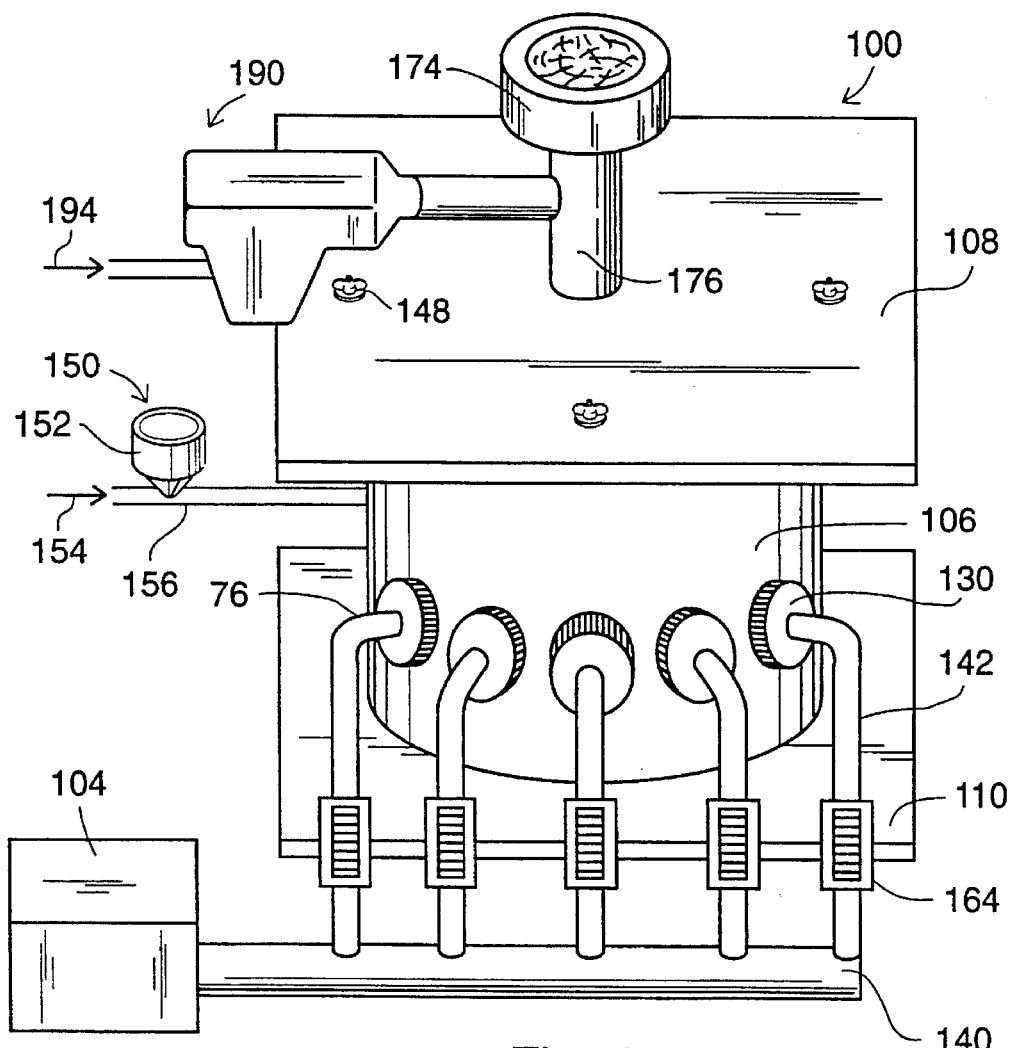
Figure 5:
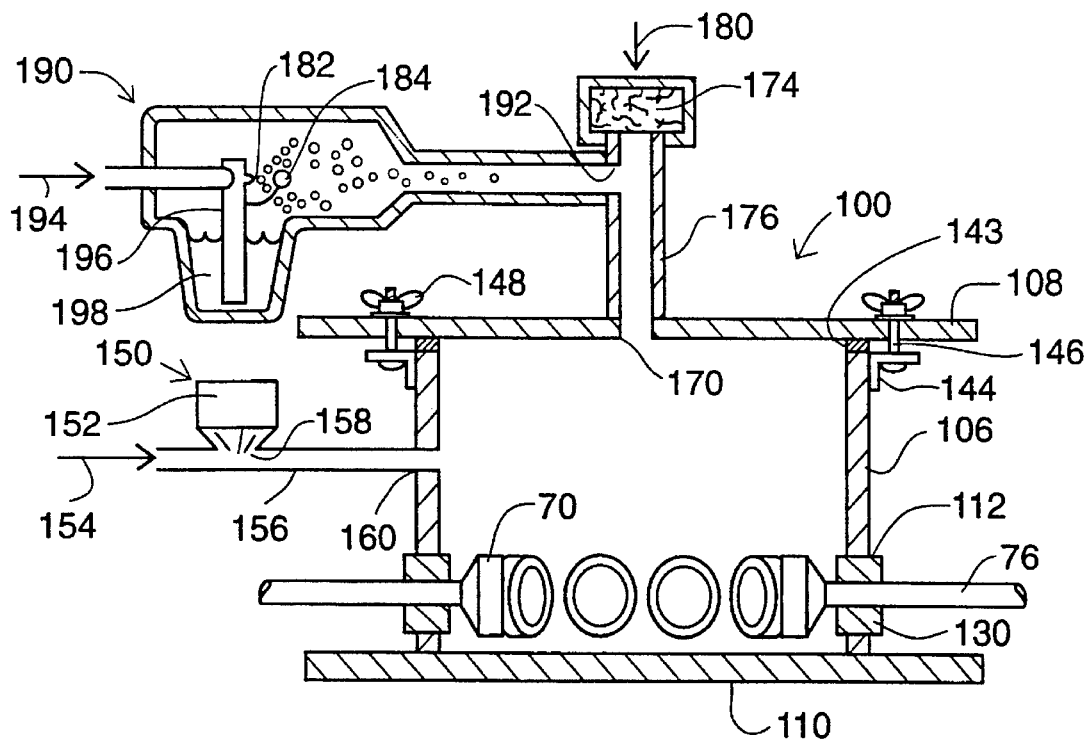
Figure 6:
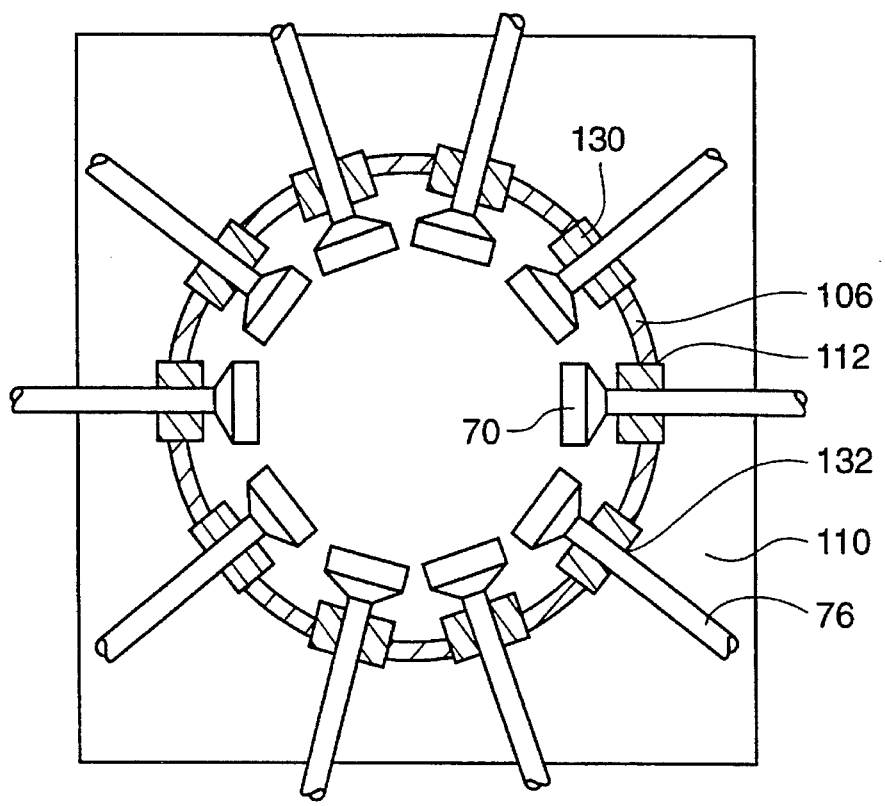

Sample holders 70 are fitted into the sampling ports 12 of container 20 using a variety of techniques. For example, securing ring 78 (FIG. 2) can be permanently affixed in port 12 and the remainder of holder 70 screwed into and screwed out of ring 78. Preferably, and as shown in FIGS. 4–6, holders 70 can be secured in ports 12 using rubber stoppers 130. A wide variety of holders and filters are available depending on specific sampling requirements.

Two 27 cfm axial fans 22 (Model 4C596, Dayton Electric, Chicago, Ill.) are positioned in the corners of container 20 near inlet 14 to mix and disperse dust and aerosol contaminants during sample collection to provide a more uniform sample distribution among the sample holders 70. Illustratively, the sampling ports 12 are fitted with 47 mm filter holders 70 (Nalgene Filter Holder 335-4000, Nalge Company, Rochester, N.Y.) to accommodate glass fiber filters 84 (Whatman GF/C). Filter holders 70 are each connected to a separate 1/16 Horsepower Air Pump, Model 4Z026 (Dayton Electric, Chicago, Ill.) with vacuum tubing (not shown). The pumping rate for each port was about 9.3–10.95 L-min$^{-1}$. The air inlet 16 at the front of container 20 is used to prevent the formation of a vacuum in container 20 since input from contaminant introduction devices through inlet 14 does not compensate for the air volume removed by the vacuum pumps.

A nebulizer setup 30 is provided for attachment to inlet 14 for introduction of an aerosol of contaminant solution into container 20. Aerosol droplet sizes ranged from 10 to 100 microns. Setup 30 consists of a pressurized air input 32 (30 psi with a flow rate of about 11 L-min$^{-1}$), a flow gage 34 (Visi-Float VFA-24-55V; Dwyer Instruments, Inc., Michigan City, Ind.) connected to nebulizer 40 (DeVilbiss Model 60 glass nebulizer, DeVilbiss Health Care Co., Somerset, Pa.), and a syringe 38 for introducing contaminant solutions and suspensions into nebulizer 40. As pressurized air 31 enters nebulizer 40 through the air inlet 42, it expands at high velocity to form fine droplets (mist) 48 by drawing liquid 44 from feed tube 46. Mist 48 is delivered to container 20 through inlet 14.

A dust generator 50 is used for the introduction of solid contaminants and co-contaminants through inlet 14. The dust generator 50 (Model MF-2 Sibata Dust Generator (MDA Scientific Inc., Glenview, Ill.) is a rotating disk type dust feeding device. The generator 50 consists of a turntable 52, a dust delivery tube 54, and a vibrating probe 59. As compressed air 57 passes through the venturi tube 56, a low pressure develops in tube 58 drawing dust from turntable 52 to container 20 through dust delivery tube 54 and inlet 14. In order to prevent the dust from adhering to the turntable, vibrating probe 59 is used during generator operation. The dust feed rate is determined by the speed of the turntable 52 and the air flow in venturi tube 56. The dust generator 50 has a flow gage 60, a pressure gage 62, a vibrating probe control 64, a turntable speed control 66, and an on/off switch 68.

Dust generator 50 and aerosol setup 30 can be used simultaneously through the use of a T-fitting 49 into inlet 14. However, when it is desirable to determine the amounts of contaminants and co-contaminants delivered from each source, the devices are used in sequence with only one device being hooked up to inlet 14 at a time. This allows each filter to be weighed before and after the use of each device to determine the amount of contaminant or co-contaminant delivered by that device.

Figure 2:
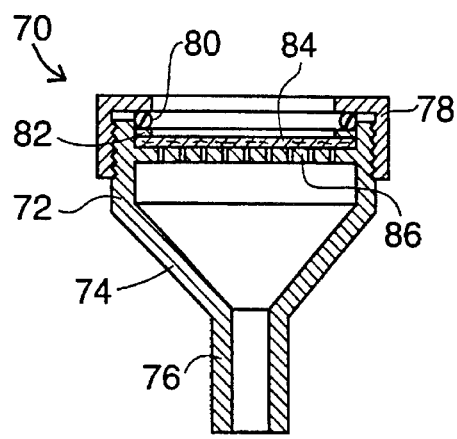
Figure 3:
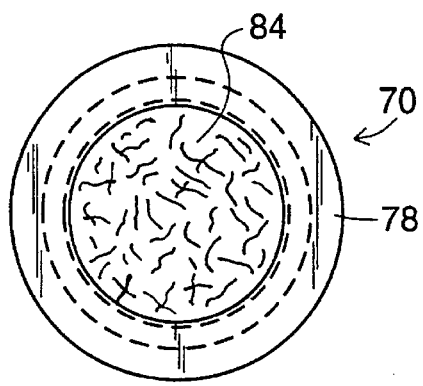

As shown in FIGS. 2 and 3, the filter holder 70 (Nalgene Filter Holder 335-4000, Nalge Company, Rochester, N.Y.) is a cylindrical tube with a cylindrical upper section 72, a frusto-conical midsection 74, and a tubular lower section 76. A perforated plate 86 is mounted in the cylindrical upper section 72 with a portion of the cylindrical upper section extending above plate 86. A holding ring 78 is releaseably secured to holder 70 by means of screw threads in holder 70 and ring 78. A resilient O-ring 80 is positioned between the filter 84 and holding ring 78 to hold the filter 84 in place in holder 70. A washer 82 is placed between O-ring 80 and filter 84. The air flow through the filter 84 is controlled by an orifice (not shown) between holder 70 and the vacuum pumps. The flow rate through each filter holder was calibrated individually using a wet test meter (Model 802, American Meter Co., Erie, Pa.). The calibrated flow rates ranged from about 9.3 to about 10.95 L-min$^{-1}$ when filter 84 is in place in holder 70.

In the alternative embodiment of the present invention shown in FIGS. 4–6, container 100 consists of a cylinder 106 with a first end (top) 108 and a second end (bottom) 110. A plurality of sampling ports 112 are arranged equidistant from each other on a circumference of cylinder 106 near one end of cylinder 106. Sample holders 70 are held in sampling ports 112 by means of resilient stoppers 130. Stoppers 130 have a center passage 132 into which the tubular portion 76 of filter holder 70 is inserted. The tubular portion 76 of the filter holder 70 is connected to vacuum manifold 140 by means of vacuum tubing 142. A flow gage and control 164 is used to monitor and control the flow rate through each filter holder 70 and filter. Vacuum manifold 140 is connected to vacuum pump 104. End 108 is secured to an end of cylinder 106 with a resilient material 143 (3M double-sided foam tape) in order to form an air-tight seal. An angle bracket 144 is attached near one end of cylinder 106. Bolts 146 pass through a hole in the angle bracket and through end 108. Wing nuts 148 secure and seal end 108 to the end of cylinder 106 and allow for easy access to the interior of container 100.

An eductor 150 (Fox Mini Eductor Series 611210, Fox Valve Development Corp., Dover, N.J.) is inserted into an aperture 160 in the cylindrical wall 106 of container 100 near the top of container 100. The top of the eductor 152 is loaded with dust or a fine powder (<200 mesh). High pressure air (indicated by arrow 154; approximately 100 psi) flows through tube 156 creating a venturi effect at eductor throat 158 which draws the dust into tube 156 where it flows into container 100.

A replacement environment 180 (typically air) for the container environment withdrawn by vacuum pump 104 enters container 100 through inlet 170. Preferably inlet 170 is located at the center of container end 108, i.e., coaxially with the axis of cylinder 106. Such placement provides an equidistant air flow path to each of the filter holders 70. Replacement air 180 is preferably filtered to remove unwanted air-borne contaminants using a suitable filter 174 (Hepa Capsule Product No. 12144; Gelman Sciences, Ann Arbor, Mich.) which is attached to container 100 by means of tubular passage 176.

A nebulized liquid can be introduced into the sampling chamber using nebulizer 190 (Retec Nebulizer; U.S. Pat. No. 3,744,722; available from Burton Medical Co., Vaneys, Calif.). Preferably nebulizer 190 is connected to passage 176. Replacement air 180 flowing past opening 192 creates a venturi effect that draws the mist from nebulizer 190 into air stream 180 and into container 100. Nebulizer 190 is connected to a pressurized air source 194 (about 15 psi) which creates a low pressure across tube 196 causing liquid contaminant 198 to be drawn upward through tube 196 where air stream 180 carries it through aperture 182 and against sphere 184 causing it to be broken into a fine mist.

The following materials and examples illustrate the testing and use of the above described devices to prepare simulated samples of protease and non-protease enzymes commonly included as components in detergent products. Such enzyme materials are known to be allergenic and a wide variety of techniques have been developed to minimize airborne enzyme dust levels in the work place. To assure compliance with government standards, it was desirable to develop analytical techniques to measure very low levels of airborne substances (0.2–0.5 ng/m$^3$ air). Since work site samples are needed for air quality monitoring, it is difficult to obtain an adequate number of air samples for new analytical method development and validation. To overcome this problem, the air sampling device of this invention was constructed and tested using a detergent enzyme as the contaminant of primary interest. The effects of non-enzyme detergent products and general atmospheric co-contaminants such as dust were also of concern, especially as to how these might relate to and effect on-site sampling and analysis when present at the work site. Although the device and methodology are illustrated for simulated enzyme samples, the device and method have applicability to the production of a wide variety of simulated samples characteristic of industrial and institutional sites such as, but not limited to, hospitals and clinics and food, consumer product, chemical, and pharmaceutical processing sites.

Contaminant dust was collected from fiberglass air filters in place on laboratory doors and office heating convectors. The dust was gently lifted from the filter surface by inverting the air filter over a sheet of brown Kraft wrap paper. The resulting loose dust was transferred from the paper into a 1 L polyethylene plastic bottle and capped. Before use, the dust was converted to a powder by gently sieving it through a 200 mesh screen with a camel hair brush. The dust powder was transferred to a 20 mL glass container with a polyethylene cap and stored at room temperature.

The enzymes Subtilisin Carlsberg (EC 3.4.21.14, ALLASE, 2.0T, NOVO Nordisk, Denmark), SAVINASE (EC 3.4.21.14, 4.0T, NOVO, Nordisk, Denmark), CELLULASE (EC 3.4.21.4, SP300, NOVO, Nordisk, Denmark), and Subtilisin BPN' (EC 3.4.21.14, Sigma Chemical Company, St. Louis, Mo.) were obtained as a prill or powder. Powder and liquid forms of laundry detergents were supplied by the Procter and Gamble Company, Cincinnati, Ohio. These detergent products did not contain enzymes and consisted of anionic surfactants, nonionic surfactants, silicate builders (powder and liquid), and perborate bleach (powder only).

EXAMPLE I

In this example, air sampling device 10 was used with the sampling container 20 fitted only with nebulizer setup 30 to test the use of nebulizer 40 as a dust delivery device. The dust generator and the fans in the chamber were not used. Tared glass fiber filters 84 (FIGS. 2 and 3) were positioned in each of the sample holders 70 which were inserted into the sampling ports 12. In a typical sample run, vacuum pumps connected to the filter holders 70 were switched on and a fine mist 48 was atomized from nebulizer 40 into container 20 impinging on the glass fiber filters 84 as the container environment was withdrawn by the vacuum pumps. After all of nebulizer solution 44 was atomized, nebulizer 40 and the vacuum pumps were stopped and the glass fiber filters 84 were removed from sample holders 70 and placed in plastic holders using nonserrated plastic-tipped forceps. The tared filters were weighed using a Mettler microbalance.

To test the use of the nebulizer for the delivery of solid contaminants and co-contaminants, dust powder at 10 mg, 50 mg, or 250 mg in 10 mL distilled water was added to nebulizer 40 using syringe 38 and the sampling device operation commenced. For the 10 mg dust/10 mL suspension, only 36% of the total mass was collected on the four filters with a mean filter weight of 0.83±0.18 mg with a coefficient of variation (CV) of 22% (Table I). The collection efficiency further decreased when the amount of dust was increased to 50 mg dust/10 mL (19.6%) and 250 mg dust/10 mL (14.4%). The low collection efficiency obtained with the configuration was due to the separation of the dust from the liquid inside the nebulizer and obstruction of the nebulizer orifice by larger dust particles.

EXAMPLE II

In this example, an alternative approach to the use of a nebulizer dust suspension was evaluated in which a enzyme-detergent solution was applied to the air filter first using nebulizer setup 30 followed by the application of dust with the Sibata dust generator 50. Container 20 was fitted with the nebulizer setup 30 for liquid delivery and dust generator 50 for dry material delivery. Fans 22 were not used. Tared glass fiber filters 84 were placed in each of the sample holders 70 which were positioned in sampling ports 12. Using syringe 38, 10 mL of an enzyme-detergent solution 44 was introduced into the nebulizer 40. The air stream to the nebulizer was started using a pressure of 30 psi and a flow rate of 11 L-min$^{-1}$. The vacuum pumps were switched on and the fine mist 48 from nebulizer 40 was collected on the glass fiber filters 84. After all of solution 44 was atomized, air flow 31 to nebulizer setup 30 was turned off and the vacuum pumps stopped and glass fiber filters 84 were removed from the sample holders 70 and placed in plastic filter holders using nonserrated plastic-tipped forceps. The tared filters were weighed using the Mettler microbalance. Filters 44 were then repositioned in their holders 70 in original sampling ports 12.

The dust generator turntable was filled with a supply of 200 mesh dust, the airflow set at 30 L-min$^{-1}$ turntable rotation speed set at 4, the vibrating probe set at 6, and the power switched on. Immediately, the vacuum pumps were switched on. Dust was delivered to container 20 and collected on glass fiber filters 84 positioned in the sampling ports 12. After collecting samples for 15 min, the dust generator 50 was switched off followed by the vacuum pumps. The glass fiber filters 84 were removed from their holders 70 and weighed to determine the gross weight of sample solution and dust using a Mettler microbalance.

This configuration significantly improved the filter weight of the air-borne contaminant samples. The mean filter weight (8.2±1.1 mg) containing enzyme, detergent, and dust increased approximately 10 fold in comparison to Example I and the % CV decreased from 22% to 13%. However, the air filters at the end of the chamber had higher weights than those on the side.

EXAMPLE III

Figure 7A:
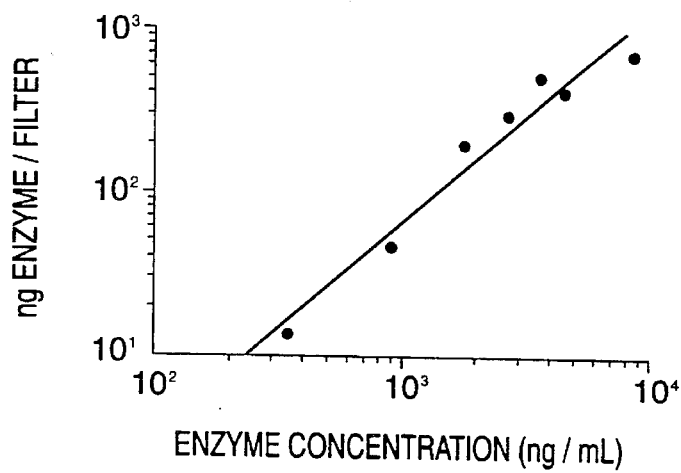
Figure 7B:
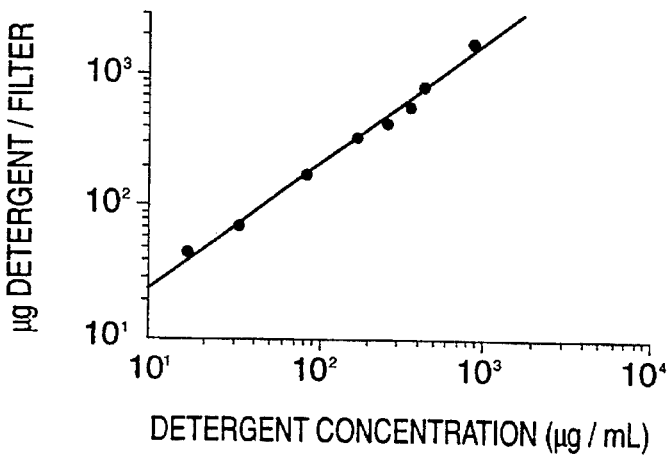
Figure 7C:
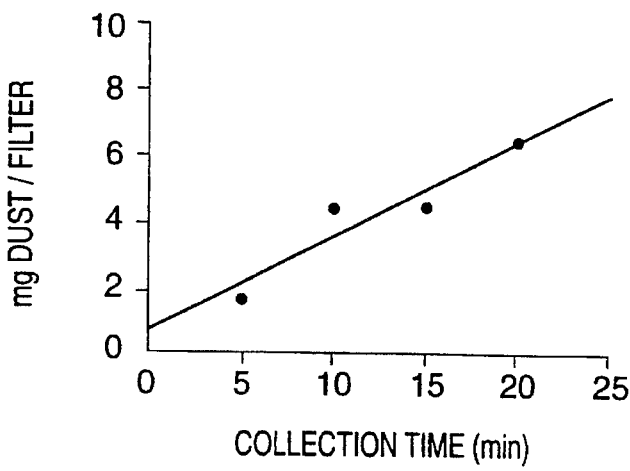

Both the nebulizer setup 30 and dust generator 50 were connected to container 20 as described in Example II. All other aspects of operation including aerosol and dust application to the glass fiber filters 84 were the same as in Example II except that two small fans 22 were positioned in the corners of the chamber near inlet tube 14 and turned on during the application of the aerosol and dust contaminant to the air filters.

The Sibata dust generator was operator for 20 minutes at an air flow of 30 L-min$^{-1}$, a tray rotational speed of 4, and vibrating probe setting of 6. The fans improved the distribution of enzyme-detergent aerosol and dust in the chamber (6.7±0.5 mg per filter) resulting in less variation between the end and side sampling ports (7% CV). This configuration was selected for generating air samples containing enzyme-detergent-dust and was further optimized to achieve levels of these components on filters similar to air samples from manufacturing sites.

TABLE I

Comparison of Air Sampling Examples I–III

| Air Sampling Example | Sample Weight[a] (mg) |
|---|---|
| I | 0.83 ± 0.18 |
| II | 8.2 ± 1.1 |
| III | 6.7 ± 0.5 |

[a]Mean and standard deviation of four replicates

EXAMPLE IV

Using the air sampling configuration described in Example 3, appropriate conditions for applying 100–1,000 ng enzyme, 100–1,000 μg detergent product, and 1–10 mg dust to glass fiber filters were determined. The detergent and enzyme were applied as solutions to the air filters using the nebulizer. The amount of detergent was monitored by weighing the tared glass fiber filters while the enzyme levels were determined by the appropriate activity assay. Since only nanogram quantities of enzyme were deposited on a filter, gravimetric analysis was not useful.

The determination of enzyme quantity was determined according to the following procedures. The air sample filters were removed from the holders, quarter folded, and placed into 50 mL conical plastic tubes using clean hands. For each sample, 10 mL of cold sample preparation buffer (500 mM sodium chloride, 20 mM Tris, 0.1% bovine serum albumin, 0.1% Tween 20, 1 mM calcium chloride, 20 mM sodium thiosulfate, and 0.1% sodium azide at pH 8.2) were added to each 47 mm filter. The sample was eluted from the glass fiber filters by rotating at 20–25 rpm for 10 min at room temperature using Cel Gro Rotator (Lab Line, Model 1640). The filter was removed with a wooden application stick. The supernatants were collected and placed on ice until use in the enzyme activity assay.

Protease enzyme activity was determined using a microwell adaptation of the procedure described by Rothgeb et al., *Journal American Oil Chemist's Society*, Vol. 65, pp. 806–810 (1988). Enzyme solutions were prepared in assay buffer containing 500 mM sodium chloride, 20 mM Tris, 0.1% Tween 20, 0.1% bovine serum albumin, and 0.1% sodium azide at pH 8.2. The chromogenic substrate, alanine-alanine-proline-phenylalanine paranitroanilide (AAPF-PNA; Sigma Chemical Co., St. Louis, Mo.), was prepared as a 200 mM solution in dimethyl sulfoxide and stored at −15° C. For the assay, 100 μL of the enzyme solution was added to a microwell plate. The AAPF-PNA substrate was diluted to a 4 mM in assay buffer and 100 μL was added to each microwell. The plate was sealed with parafilm and incubated at 37° C. for 2 hrs. with Subtilisin Carlsberg for 6 hrs. with Subtilisin BPN', and for 18 hrs. with SAVINASE. The reaction was stopped by adding 50 μL of 1M sodium acetate, pH 4.0. The absorbance at 405 nm was determined using the plate reader system described above. Enzyme concentrations of samples were calculated from calibration curves of enzyme standards. A chromogenic substrate assay for cellulase activity was based on the method described by Claeyssens in *Biochemistry and Genetics of Cellulose Degradation*, edited by Aubert et al, New York: Academic Press, 1988, pp. 393–396. Protein content of the protein substrates used in the above enzyme determinations were determined using a conventional Lowry method, *Journal Biological Chemistry*, Vol. 193, pp. 265–275 (1951).

Various concentrations of detergent and enzyme at 100:1 ratio (w/w) were prepared in distilled water and 10 mL of the solution were introduced into nebulizer 40. The air flow to nebulizer 40 and the vacuum pumps attached to the filter holders 70 were turned on and air sampling was performed. The expected level of enzyme (100–1,000 ng/filter) was achieved using a 1769 ng enzyme/mL solution (FIG. 7A) and for detergent, 100–1000 μg was obtained with a 88 μg/mL solution (FIG. 7B). The recovery for the aerosol solutions was 1–5% for enzyme and 2–10% for detergent product.

Although the aerosol should ideally contact the air filter by following the air stream from the nebulizer to the sampling ports, some of the aerosol particles may have been below the filter collection size (<1 μm diameter) or may have settled by gravity or deposited diffusively on the chamber surfaces due to turbulence in the chamber disrupting this air stream. A significantly higher amount of enzyme was required to achieve the target level than for the detergent product. This effect may also be attributed to differential aerosolization rates due to the size or surface tension properties of the detergent aerosol particles in comparison to those containing enzyme protein.

The dust collection on the filters was studied by varying the Sibata dust generator operating time. Air samples were collected for 5, 10, 15, or 20 minutes using the described turntable speed, air flow, and vibrating probe setting for the dust generator and with the chamber fans operating. Approximately 7 mg of dust was collected on each filter after 20 minutes (FIG. 7C).

EXAMPLE V

The reproducibility and versatility of this device for simulating air samples from manufacturing sites was determined by preparing air filters using four enzyme-detergent combinations. The configuration given in Example III was used with an aerosol solution 44 containing 1769 ng/mL enzyme and 88 μg/mL detergent and a 20 minute collection time for dust contaminant sample preparation. Sixty air filters were prepared for Subtilisin Carlsberg and Subtilisin BPN' with liquid detergent and SAVINASE and CELLULASE with powder detergent. The air samples were prepared for each combination including dust and then each filter was analyzed for enzyme, detergent product, and dust content. The enzyme amount was determined in the activity assay for the appropriate enzyme while the amount of detergent product and dust was determined gravimetrically. The levels ranged from 72 ng to 457 ng for the enzymes, 256 μg for the detergent products, and 5.6 mg to 7.9 mg for the dust as shown in Table II. Actual sample collections obtained by high volume samplers at a typical detergent manufacturing site ranged between 100–1000 ng total enzyme, 100–1000 μg total detergent, and 1–10 mg total dust.

TABLE II

| | Reproducibility of Air Sampling System | | | |
|---|---|---|---|---|
| Enzyme | Detergent Type | Enzyme Weight[a] | Detergent Weight[b] | Dust Weight[c] |
| Subtilisin Carlsberg | Powder | 170 ± 24 (53) | 536 ± 64 | 7.2 ± 1.9 |
| Subtilisin BPN' | Liquid | 389 ± 34 (24) | 247 ± 34 | 5.6 ± 1.3 |
| SAVINASE | Powder | 72 ± 16 (49) | 1115 ± 168 | 7.9 ± 1.6 |
| CELLULASE | Powder | 457 ± 128 (28) | 256 ± 43 | 6.0 ± 1.6 |

[a]Data represents mean ± standard deviation for ng enzyme per filter. Parenthesis indicates number of samples tested.
[b]Data represents mean ± standard deviation for μg detergent applied to 60 glass fiber filters.
[c]Data represents mean ± standard deviation for mg of dust applied to 60 glass fiber filters.

EXAMPLE VI

The air sampling configuration shown in FIGS. 2–6 was used to collect simulated samples. Filters 84 were first weighed and placed in holders 70 and inserted into inlet ports 112. A detergent was dissolved in water and placed in nebulizer 190. Vacuum pump 104 was turned on and a 15 psi air source 194 connected to nebulizer 190. After the detergent solution was completely nebulized, the air source 194 to the nebulizer was disconnected and the vacuum pump 104 turned off. Filters 84 were removed and weighed. A second set of filters 84 was then placed in holders 70. A small portion of a known quantity of dust was placed in eductor 150, vacuum pump 104 started, and a 100 psi air source 154 connected to the eductor. The dust was added a little at a time over the course of about ½ hour of operation. After all of the dust had passed through the eductor, air source 154 was removed and vacuum pump 104 turned off. The second set of filters 84 were removed and weighed. A third set of filters 84 was placed in holders 70. An enzyme contaminant was dissolved in a buffer solution and placed in the nebulizer. The vacuum pump 104 was stated and a 15 psi air supply 194 connected to nebulizer 190. After the enzyme solution was completely nebulized, air supply 194 was removed and the vacuum pump 104 turned off. Filters 84 were removed and the enzyme content was determined according to the methods given in our co-pending application, Ser. No. 08/175,715 filed Dec. 30, 1993 all of which is incorporated herein by reference as if completely written herein. The enzyme content could have also been determined using the methods given in Example IV. Results from the three sets of filters are given in Table III.

TABLE III

| | Cylindrical Container | | |
|---|---|---|---|
| Filter # | Detergent (liquid Tide) μg | Dust mg | Enzyme ng |
| 1 | 110 | 5.1 | 284 |
| 2 | 200 | 5.0 | 293 |
| 3 | 150 | 5.0 | 271 |
| 4 | 140 | 5.3 | 243 |
| 5 | 240 | 5.1 | 270 |
| 6 | 250 | 5.1 | 249 |
| 7 | 190 | 5.3 | 234 |
| 8 | 140 | 5.3 | 262 |
| 9 | 150 | 5.1 | 269 |
| 10 | 100 | 5.1 | 229 |
| Collection Efficiency | 34.8% | 8.45% | 42% |
| Coeff. of Variation | 30.7% | 2.28% | 8.11% |

Collection efficiency is defined as the amount of contaminant collected on the filters divided by the amount of contaminant introduced into the container times 100.

It is possible that changes in configurations to other than those shown could be used but that which is shown if preferred and typical. Without departing from the spirit of this invention, various means of fastening the components together may be used.

It is therefore understood that although the present invention has been specifically disclosed with the preferred embodiment and examples, modifications to the design concerning sizing and shape will be apparent to those skilled in the art and such modifications and variations are considered to be equivalent to and within the scope of the disclosed invention and the appended claims.

We claim:

1. An air sampling device for producing a contaminant test sample for use in development, testing, and validation of analytical detection and analysis methodology, said device comprising a sampling container having:

a. a container environment contained therein;

b. a contaminant introduction inlet means for introducing an air-borne contaminant and a co-contaminant into said container environment;

c. a sample collection port means for collecting said air-borne contaminant and said co-contaminant from said container environment to afford said contaminant test sample; and d. a replacement environment inlet means for entry of a replacement environment into said sampling container.

2. The device according to claim 1 further comprising a filter means attached to said container for removing unwanted contaminants from said replacement environment.

3. The device according to claim 1 further comprising means for opening and closing said sampling container so as to allow access to the interior of said container.

4. The device according to claim 1 further comprising an injector attached to said container for contaminant introduction through said contaminant introduction inlet means.

5. The device according to claim 4 wherein said injector is an eductor.

6. The device according to claim 4 wherein said injector is a nebulizer.

7. The device according to claim 4 wherein said injector is a dust generator.

8. The device according to claim 1 further comprising a first injector attached to said container for liquid contaminant introduction through said contaminant introduction inlet means and a second injector attached to said container for solid contaminant introduction through a second contaminant introduction inlet.

9. The device according to claim 1 further comprising a sample collection holder means attached to said container for collecting said contaminant test sample from said sample collection port means.

10. The device according to claim 9 with said sample collection holder means having a passage therethrough and comprising:
   a. a cylindrical upper section;
   b. a frusto-conical midsection;
   c. a tubular lower section;
   d. a perforated plate mounted in said cylindrical upper section for supporting a filter with a portion of said cylindrical upper section extending above said plate;
   e. a holding ring releasably secured to said holder means; and
   f. a resilient O-ring placed between said filter and said holding ring.

11. The device according to claim 10 further comprising a nonstick circular flat washer placed between said O-ring and said filter.

12. The device according to claim 10 wherein said sample collection holder means is attached to said container by means of a resilient stopper.

13. The device according to claim 1 with said sampling container comprising a cylinder with closed ends.

14. The device according to claim 13 wherein at least one of said ends is removable and attached to said cylinder using an intervening resilient sealing material.

15. The device according to claim 13 with a plurality of said sample collection port means arranged around a circumference of said cylinder equidistant from each other and near one of said cylinder ends.

16. The device according to claim 15 wherein said replacement environment inlet means is located in said cylinder end opposite said end near said plurality of said sample collection port means.

17. The device according to claim 16 further comprising a replacement environment filter attached to said container to remove unwanted contaminants from said replacement environment.

18. The device according to claim 15 further comprising a flow regulator for regulating the flow of said container environment through said plurality of said sample collection port means.

19. The device according to claim 1 further comprising a vacuum pump for withdrawing said container environment from said sampling container.

20. The device according to claim 1 further comprising a flow regulator means for regulating the flow of said container environment from said sampling container.

21. The device according to claim 1 further comprising a fan for circulating and mixing at least one of said contaminant and said co-contaminant with said container environment.

22. An air sampling device for producing a contaminant test sample for use in development, testing, and validation of analytical detection and analysis methodology, said device comprising:
   a. a sampling container;
   b. a container environment contained in said container;
   c. a connector means attached to said container and serving as a common passage for entry of a contaminant and a replacement environment into said container;
   d. an injector means attached to said connector means for introducing a contaminant into said container environment through said common passage;
   e. a filter means attached to said container for collecting a contaminant test sample from a mixture of said contaminant and said container environment;
   f. a pump means attached to said container for moving said contaminant and said container environment through said filter means so as to collect said contaminant test sample on said filter;
   g. a container inlet means to allow a replacement environment and a contaminant to enter said container through said connector means; and
   h. an inlet filter means attached to said connector means for removing unwanted impurities from said replacement environment.

23. The air sampling device of claim 22 wherein said injector means is a nebulizer.

24. The air sampling device of claim 22 further comprising a second injector means attached to said container for introducing a co-contaminant into said container environment.

25. The air sampling device of claim 24 wherein said injector means is a nebulizer and said second injector means is an eductor.

26. A method of preparing a contaminant test sample for use in development, testing, and validation of analytical detection and analysis methodology, said method comprising:
   a. simultaneously
      1) removing a container environment through a filter;
      2) adding a replacing environment to said container;
   b. adding a contaminant to and mixing said contaminant with said container environment while said container environment is being withdrawn and replaced;
   c. continuing to withdraw said container environment from said container through said filter after said contaminant has been added until said contaminant test sample is collected.

27. The method according to claim 26 further comprising the step of filtering said replacing environment prior to adding to said container.

28. The method of claim 26 wherein said contaminant is a liquid.

29. The method of claim 26 wherein said contaminant is a solid.

30. The method of claim 26 further comprising the step of adding a co-contaminant to and mixing said co-contaminant with said container environment while said container environment is being withdrawn and replaced.

* * * * *